United States Patent
Kulig et al.

(10) Patent No.: US 11,440,877 B2
(45) Date of Patent: Sep. 13, 2022

(54) SILANE DISULFIDE VEGETABLE OILS, METHOD OF MAKING AND USE IN RUBBER COMPOSITIONS AND TIRES

(71) Applicant: The Goodyear Tire & Rubber Company, Akron, OH (US)

(72) Inventors: Joseph John Kulig, Tallmadge, OH (US); Kelsey Elizabeth Cantwell, Akron, OH (US); Frank James Feher, Copley, OH (US); Thomas Franklin Spilker, Broadview Heights, OH (US); George Jim Papakonstantopoulos, Medina, OH (US)

(73) Assignee: The Goodyear Tire & Rubber Company, Akron, OH (US)

( * ) Notice: Subject to any disclaimer, the term of this patent is extended or adjusted under 35 U.S.C. 154(b) by 312 days.

(21) Appl. No.: 16/671,271

(22) Filed: Nov. 1, 2019

(65) Prior Publication Data

US 2021/0130553 A1    May 6, 2021

(51) Int. Cl.
```
C07C 319/22    (2006.01)
C07C 321/12    (2006.01)
C07F 7/18      (2006.01)
C08H 3/00      (2006.01)
C08L 91/02     (2006.01)
B60C 1/00      (2006.01)
C08L 9/06      (2006.01)
C08L 23/22     (2006.01)
C11B 1/10      (2006.01)
C11B 3/02      (2006.01)
```

(52) U.S. Cl.
CPC ............. *C07C 321/12* (2013.01); *B60C 1/00* (2013.01); *C07C 319/22* (2013.01); *C07F 7/1804* (2013.01); *C08H 3/00* (2013.01); *C08L 9/06* (2013.01); *C08L 23/22* (2013.01); *C08L 91/02* (2013.01); *C11B 1/108* (2013.01); *C11B 3/02* (2013.01)

(58) Field of Classification Search
CPC .. C08H 3/00; B60C 1/00; C08L 91/02; C07C 321/12; C07C 319/22; C07C 323/52
See application file for complete search history.

(56) References Cited

U.S. PATENT DOCUMENTS

| | | |
|---|---|---|
| 3,476,826 A | 11/1969 | Millen |
| 4,039,586 A | 8/1977 | Shasha et al. |
| 4,512,926 A | 4/1985 | Kampf et al. |
| 5,395,891 A | 3/1995 | Obrecht et al. |
| 5,512,190 A | 4/1996 | Anderson et al. |
| 5,672,639 A | 9/1997 | Corvasce et al. |
| 6,127,488 A | 10/2000 | Obrecht et al. |
| 6,133,364 A | 10/2000 | Obrecht et al. |
| 6,207,757 B1 | 3/2001 | Obrecht et al. |
| 6,242,534 B1 | 6/2001 | Obrecht et al. |
| 6,359,046 B1 | 3/2002 | Cruse |
| 6,372,857 B1 | 4/2002 | Obrecht et al. |
| 6,608,125 B2 | 8/2003 | Cruse et al. |
| 7,521,401 B2 | 4/2009 | Rowland |
| 9,238,588 B2 | 1/2016 | Harrington et al. |
| 9,550,850 B2 | 1/2017 | Sato et al. |
| 10,005,857 B2 | 6/2018 | Kloppenburg et al. |
| 10,245,234 B1 | 4/2019 | Lele |
| 2003/0130535 A1 | 7/2003 | Deschler et al. |
| 2006/0235120 A1 | 10/2006 | Saiki et al. |
| 2009/0076279 A1 | 3/2009 | Rowland et al. |
| 2009/0292054 A1 | 11/2009 | Omura et al. |
| 2010/0083871 A1 | 4/2010 | Narayan et al. |
| 2012/0064322 A1 | 3/2012 | Upshaw et al. |
| 2014/0194567 A1* | 7/2014 | Narayan ................ C08G 77/38 524/588 |
| 2014/0335032 A1 | 11/2014 | Panandiker et al. |
| 2014/0335167 A1 | 11/2014 | Panandiker et al. |
| 2015/0166701 A1 | 6/2015 | Chisholm et al. |
| 2020/0377702 A1 | 12/2020 | Schoeffel et al. |

FOREIGN PATENT DOCUMENTS

| | | |
|---|---|---|
| CN | 105713700 B | 8/2018 |
| GB | 455779 A | 10/1936 |
| JP | 2014177431 A | 9/2014 |

OTHER PUBLICATIONS

Tambe Chetan et al, Silylation of Non-Terminal Double Bonds of Natural Oils, Silylation of Non-Terminal Double Bonds of Natural Oils, Jun. 12, 2015 (Jun. 12, 2015), 87-98, vol. 8, No. 1, Silicon, East Lansing, US.

European Search Report for Serial No. EP20204370 dated May 3, 2021.

Bhaumik et al., Rapid Transformation of Alkyl Halides into Symmetrical Disulfides Using Sodium Sulfide and Carbon Disulfide, SynOpen, 1, 2017, pp. 117-120, Georg Thieme Verlag Stuttgart, New York.

Ionescu et al., Functionalized vegetable oils as precursors for polymers by thiol-ene reaction, European Polymer Journal 67, 2015, pp. 439-448, Elsevier Ltd.

Kuhlmann et al., Cysteine-Functional Polymers via Thiol-ene Conjugation, Macromol. Rapid Commun., 2015, 472-476, 36, Wiley-VCH Verlag GmbH & Co. KGaA, Weinheim.

Li et al., Modified soybean oil-extended SBR compounds and vulcanizates filled with carbon black, Polymer, Jan. 13, 2015, pp. 144-156, 60, Elsevier Ltd.

Mehta et al., Moderate Temperature Curing of Plant Oils with Bismaleimides via the Ene Reaction, Ind. Eng. Chem. Res., Oct. 13, 2016, https://pubs.acs.org/doi/pdf/10.1021/acs.iecr.6b03004, 55, 45, American Chemical Society.

Nalawade et al., Modified soybean oil as a reactive diluent: coating performance, Journal of Coatings Technology and Research, Jun. 11, 2015, pp. 1005-1021, 12, American Coatings Association.

Nalawade et al., Modified soybean oil as a reactive diluent: Synthesis and characterization, Polymer Chemistry, Aug. 24, 2014, Journal of Polymer Science.

(Continued)

*Primary Examiner* — Yate' K Cutliff
(74) *Attorney, Agent, or Firm* — Mandy B. Willis

(57) ABSTRACT

The present invention is directed to novel silane disulfide vegetable oils, a method of making the oils, their use in rubber compositions, and their use in tires.

17 Claims, No Drawings

(56) References Cited

OTHER PUBLICATIONS

Shibata et al., High Performance Bio-Based Thermosetting Resins Composed of Tung Oil and Bismaleimide, Journal of Applied Polymer Science, Feb. 5, 2010, pp. 896-901, 119(2), Wiley Periodicals, Inc.
Shibata et al., High-performance bio-based bismaleimide resins using succinic acid and eugenol, Polymer Journal, Sep. 14, 2011, pp. 916-922, 43, The Society of Polymer Science, Japan.
Yoon et al., Self-Healing Polymer Films Based on Thiol—Disulfide Exchange Reactions and Self-Healing Kinetics Measured Using Atomic Force Microscopy, Macromolecules, Dec. 16, 2011, pp. 142-149, 45, 1, American Chemical Society.

\* cited by examiner

SILANE DISULFIDE VEGETABLE OILS, METHOD OF MAKING AND USE IN RUBBER COMPOSITIONS AND TIRES

BACKGROUND

The benefit of including one or more reinforcing fillers in rubber formulations has long been appreciated. To attain needed performance characteristics, carbon black has been widely used in making rubber formulations for use in a wide variety of rubber products, such as tires, power transmission belts, conveyor belts, hoses, air springs, and the like, for many decades. Reinforcing silicas, including, but not limited to, rice hulled ash silica and chemically modified silicas, are also widely used in a variety of industrial products. Non-reinforcing and semi-reinforcing fillers, such as clay, talc, lignin, diatomaceous earth, calcium carbonate, titanium dioxide, aluminum-trihydrate, and the like, have also been used in making a wide variety of rubber products. For over 25 years silica has been employed as a reinforcing filler in conjunction with carbon black in tire tread compounds.

In recent years the use of silica as a reinforcing agent in rubber formulations has grown significantly in importance. In fact, today silica is widely used in rubber formulations as a replacement, or more typically a partial replacement, for carbon black in rubber articles, such as tires. This is because silica reinforcement offers numerous benefits over conventional compounding with carbon black. More specifically, the utilization of silica in tire tread formulations is believed to (a) lower rolling resistance, (b) provide better traction on wet surfaces and snow, and (c) lower noise generation, when compared with conventional tires filled with carbon black.

Sometimes rubber for tires is supplied by a rubber producer to a tire manufacturer in the form of a masterbatch containing an elastomer, an oil extender, and a filler. The traditional filler has been carbon black in the form of fine particles. These particles have hydrophobic surface characteristics and will therefore disperse easily within the hydrophobic elastomer. In contrast, silica has a very hydrophilic surface and considerable difficulty has been encountered in dispersing silica in the hydrophobic rubbery elastomer.

To improve dispersion of the silica during dry mixing, it has been proposed that such compounding operations employ a silica which has been treated with an organosilane coupling agent having dual functionality. Representative of such coupling agents are those well-known compounds that include both an organic group, such as an amino alkyl group, a mercaptoalkyl group, or a polysulfidic-bis-organo alkoxy silane group bonded directly to the silicon atom along with a readily hydrolyzable group, such as an alkoxy group as represented by a methoxy group or an ethoxy group, likewise bonded directly to the silicon atom. In those systems, it is generally recognized that the alkoxy group hydrolyzes in the presence of moisture typically found on the surface of the silica to form the corresponding silanol which reacts with or condenses in the presence of the silica surface to bond the silicon atom to the silica surface. The organic groups likewise attached to the silicon atom are thus available for chemical reaction with the polymer matrix during vulcanization. As a result, the polymer matrix may become chemically bonded by means of the coupling agent to the silica surface during cure or vulcanization of the polymer. Problems associated with the use of such silanes during compounding are unpleasant odors, premature curing, and/or scorching.

It is well known that mercaptosilanes offer excellent coupling between rubber and silica, resulting in rubber compounds for tire treads with improved wet and ice skid resistance, rolling resistance and treadwear even at low loadings. However, the high reactivity of mercaptosilanes makes it impractical to use such silane coupling agents in applications where conventional Banbury mixing is employed. In cases where mercaptosilane coupling agents are used in silica compounds, it is important to maintain low temperatures (120° C. to 145° C.) to avoid premature crosslinking which proves to be a problem at higher temperatures. However, low mixing temperatures result in a marked reduction in the mechanical efficiency of mixing that is essential for an optimum dispersion of the silica. The longer mixing time at a low temperature results in a significant reduction in mixing productivity which in turn increases expense. Another drawback of using low temperatures for mixing without extended mixing duration is that less completed silanization occurs which results in the release of ethanol in downstream operations giving rise to porosity from the extrudate and reduced extrusion rates.

There continues to be a long felt need for silica filled rubber formulations that process better (have better extrusion quality) and which exhibit a higher level of dynamic stiffness. However, it is important for these objectives to be attained without compromising other desirable attributes of the silica filler rubber formulation, such as maintaining a low level of hysteresis. The use of silica reinforced tire tread compounds containing organofunctional silanes as coupling agents results in substantial performance benefits, including lower hysteresis and improved wet and ice traction. Unfortunately, these improvements in performance are usually accompanied by difficult tread compound processing due to high Mooney viscosity and reduced tire handling performance due to low dynamic stiffness at low strains of the cured rubber tread. Typical polysulfide silanes used in silica filled tire treads serve to hydrophobate the silica surface, reducing the silica "filler-filler" network resulting in a reduction of dynamic stiffness at low strain levels of the compound. Blocked mercaptosilanes (e.g., 3-octanoylthio-1-propyltriethoxysilane) further amplify this effect. Unlike silica filled tire tread compounds containing polysulfide silanes or blocked mercaptosilanes, carbon black filled tread compounds have high levels of dynamic stiffness at low strain due to the inherent "filler-filler" network formed by the carbon black. This high level of dynamic stiffness at low strain is advantageous for improved tire handling performance. However, this carbon black network also results in a substantial increase in hysteresis as compared to the silica/silane containing tread compounds. Furthermore, the high Mooney viscosity of the silica filled tire tread compounds often require the inclusion of a process additive that reduces the compound viscosity but also further reduces the low strain dynamic stiffness of the cured silica tread compound. Since low strain stiffness of the cured tread compound is a very important parameter for tire handling performance and since process additives reduce low strain dynamic stiffness, a way to increase in the low strain stiffness of a silica filled tread compound without a substantial detrimental increase in hysteresis is needed.

SUMMARY

The present invention is directed to a vegetable oil derivative comprising the structure

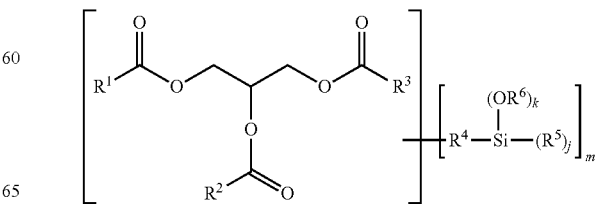

where $R^1$, $R^2$ and $R^3$ are independently C15-C20 alkenyl, C15-C20 alkyl, and optionally containing aromatic groups; $R^4$ is —S—S—$R^7$— or $R^4$ is —S—X—S—S—$R^7$— where X is substituted or unsubstituted C1 to C10 alkane diyl, substituted or unsubstituted phenylene, or a combination thereof; $R^5$, $R^6$ are independently C1 to C10 alkyl, $R^7$ is C1 to C10 alkane diyl, j=0 to 2, k=1 to 3, and j+k=3; wherein each $R^4$ is attached via a carbon-sulfur linkage to one of $R^1$, $R^2$ or $R^3$; and m is the number of the carbon-sulfur linkages.

The invention is further directed to a method of making the vegetable oil derivative, a rubber composition and a pneumatic tire.

DESCRIPTION

There is disclosed a vegetable oil derivative comprising the structure

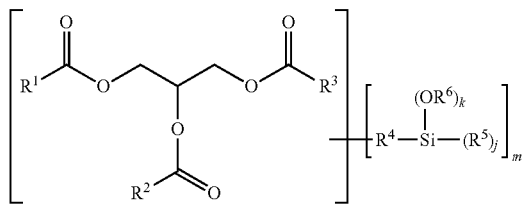

where $R^1$, $R^2$ and $R^3$ are independently C15-C20 alkenyl, C15-C20 alkyl, and optionally containing aromatic groups; $R^4$ is —S—S—$R^7$— or $R^4$ is —S—X—S—S—$R^7$— where X is substituted or unsubstituted C1 to C10 alkane diyl, substituted or unsubstituted phenylene, or a combination thereof; $R^5$, $R^6$ are independently C1 to C10 alkyl, $R^7$ is C1 to C10 alkane diyl, j=0 to 2, k=1 to 3, and j+k=3; wherein each $R^4$ is attached via a carbon-sulfur linkage to one of $R^1$, $R^2$ or $R^3$; and m is the number of the carbon-sulfur linkages.

The vegetable oil derivative may be produced by modification of a triglyceride.

In various embodiments, the vegetable oil derivative may be produced via disulfide exchange with modified triglyceride containing at least one thiol group (—SH, also known as mercapto or sulfanyl,) otherwise referred to herein as a thiolized or mercaptanized triglyceride.

Triglyceride Starting Material has the General Structure

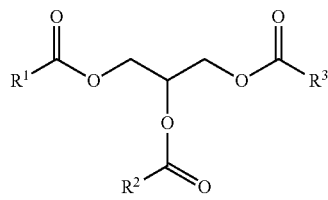

where $R^1$, $R^2$, and $R^3$ are as defined previously. Suitable triglycerides include vegetable oils and their derivatives, preferably soybean oil. One or more of groups $R^1$, $R^2$, and $R^3$ must contain at least one olefin bond.

In one embodiment, the triglyceride is a vegetable oil. Suitable vegetable oils include those with olefinic unsaturation in their fatty acid chains, including but not limited to soybean oils, canola oils, castor oils, palm oils, coconut oil, and corn oils. In one embodiment, the triglyceride is a high oleic soybean oil, containing about 75 percent by weight of oleic acid residues as oleyl chains.

In one embodiment, the thiolized triglyceride is produced via a thiol-ene reaction of a dithiol with the triglyceride. For the thiol-ene reaction, dithiols are used of the general structure

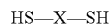

where X is substituted or unsubstituted C1 to C10 alkane diyl, substituted or unsubstituted phenylene, or a combination thereof, including substructures containing other functionalities, including alcohols, carbonyls, carboxylic acids, esters, anhydrides, amines, amides, amino acids, imines, or halides. In one embodiment, the dithiol is of the structure

where n=1-12, preferably 3-6, and most preferably 6. Reaction of the dithiol with the triglyceride provides free thiol functionality on the thiol-modified triglyceride for subsequent reactivity.

The thiol-ene reaction between a dithiol and olefinic unsaturation of the triglyceride to produce a thiolized triglyceride may proceed as follows

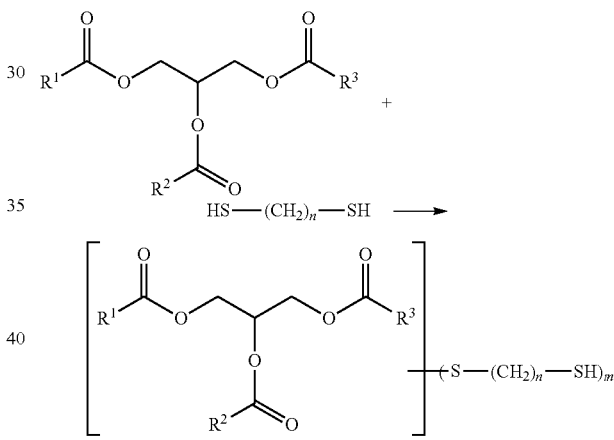

where m is the number of dithiol residues covalently bonded to a carbon atom of one of $R^1$, $R^2$ or $R^3$ resulting from the thiol-ene reaction. The olefin-containing triglyceride may be partially or fully functionalized with free thiols via thiol-ene reaction, depending on the reaction conditions to give the general structure above of a thiolized triglyceride.

Alternatively, the thiolized triglyceride is produced via direct addition of $H_2S$ to the triglyceride to produce a mercaptanized triglyceride:

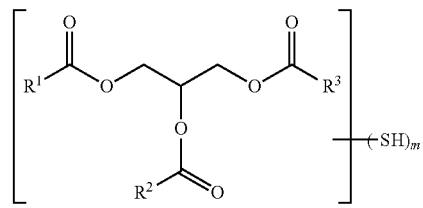

where each thiol group —SH is covalently bonded to a carbon atom of one of $R^1$, $R^2$ or $R^3$. In one embodiment, the thiolized triglyceride is a mercaptanized soybean oil such as that commercially available as Polymercaptan 358 from Chevron Phillips.

A silane disulfide may be used in a disulfide exchange reaction with the thiolized triglyceride to produce a silane disulfide triglyceride. In one embodiment, the silane disulfide is of formula

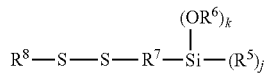

where, $R^4$, $R^5$, $R^6$, $R^7$, k, and j are as previous, and $R^8$ is an organic leaving group. In one embodiment, $R^8$ is a benzothiazyl group. The silane disulfide may be obtained by disulfide exchange reaction of a mercaptoalkylsilane with a bisorganodisulfide, for example reaction of (3-mercaptopropyl)triethoxysilane with benzothiazole disulfide (2,2'-dithiobis-benzothiazole) to produce 2-[[3-triethoxysilyl)propyl]dithio]benzothiazole. In one embodiment, the thiolized triglyceride resulting from reaction of a triglyceride with a dithiol may be used in a subsequent disulfide exchange with the silane disulfide as follows:

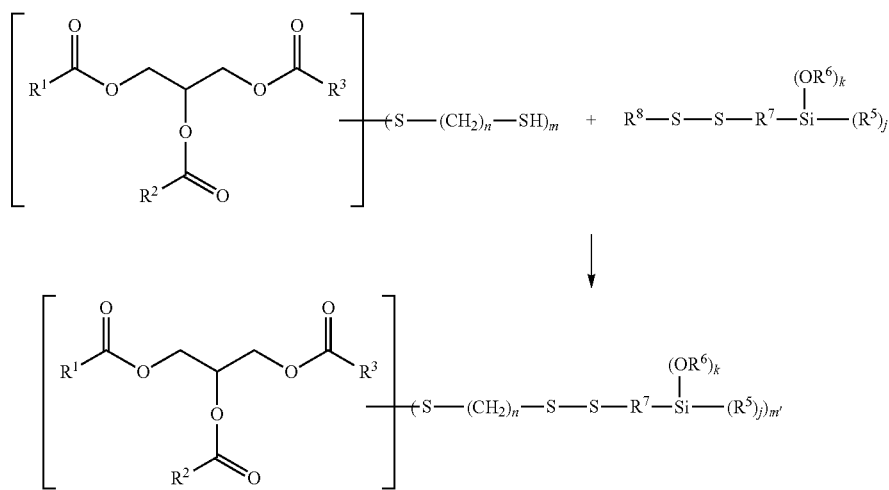

where m' is m is the number of the silane disulfide pendant to the triglyceride. In another embodiment, the thiolized triglyceride resulting from reaction of a triglyceride with $H_2S$ may be used in a disulfide exchange with the silane disulfide as follows:

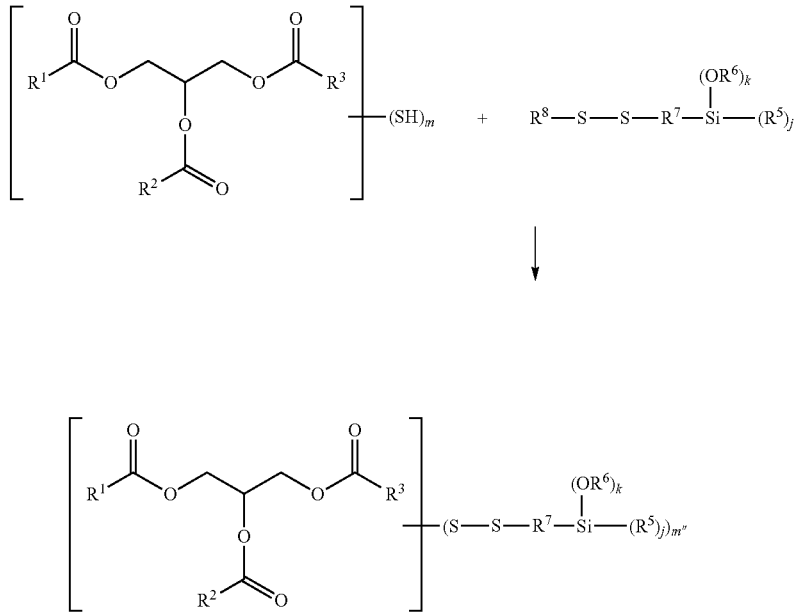

where m" is the number of the silane disulfide groups pendant to the triglyceride. Such disulfidic triglyceride may be a vegetable oil derivative in embodiments where the triglyceride is a vegetable oil.

In one embodiment, the functional oil is a soybean oil functionalized with propyltriethoxysilyl disulfide, where the silane disulfide content can vary from 1-8 substituents per triglyceride molecule.

The vegetable oil derivative may be used in a vulcanizable rubber composition. In one embodiment, the vegetable oil derivative is used in an amount ranging from 1 to 80 phr.

The rubber composition may include, in addition to the vegetable oil derivative, one or more rubbers or elastomers containing olefinic unsaturation. The phrases "rubber or elastomer containing olefinic unsaturation" or "diene based elastomer" are intended to include both natural rubber and its various raw and reclaim forms as well as various synthetic rubbers. In the description of this invention, the terms "rubber" and "elastomer" may be used interchangeably, unless otherwise prescribed. The terms "rubber composition," "compounded rubber" and "rubber compound" are used interchangeably to refer to rubber which has been blended or mixed with various ingredients and materials and such terms are well known to those having skill in the rubber mixing or rubber compounding art. Representative synthetic polymers are the homopolymerization products of butadiene and its homologues and derivatives, for example, methylbutadiene, dimethylbutadiene and pentadiene as well as copolymers such as those formed from butadiene or its homologues or derivatives with other unsaturated monomers. Among the latter are acetylenes, for example, vinyl acetylene; olefins, for example, isobutylene, which copolymerizes with isoprene to form butyl rubber; vinyl compounds, for example, acrylic acid, acrylonitrile (which polymerize with butadiene to form NBR), methacrylic acid and styrene, the latter compound polymerizing with butadiene to form SBR, as well as vinyl esters and various unsaturated aldehydes, ketones and ethers, e.g., acrolein, methyl isopropenyl ketone and vinylethyl ether. Specific examples of synthetic rubbers include neoprene (polychloroprene), polybutadiene (including cis-1,4-polybutadiene), polyisoprene (including cis-1,4-polyisoprene), butyl rubber, halobutyl rubber such as chlorobutyl rubber or bromobutyl rubber, styrene/isoprene/butadiene rubber, copolymers of 1,3-butadiene or isoprene with monomers such as styrene, acrylonitrile and methyl methacrylate, as well as ethylene/propylene terpolymers, also known as ethylene/propylene/diene monomer (EPDM), and in particular, ethylene/propylene/dicyclopentadiene terpolymers. Additional examples of rubbers which may be used include alkoxy-silyl end functionalized solution polymerized polymers (SBR, PBR, IBR and SIBR), silicon-coupled and tin-coupled star-branched polymers. The preferred rubber or elastomers are polyisoprene (natural or synthetic), polybutadiene and SBR.

In one aspect the at least one additional rubber is preferably of at least two of diene based rubbers. For example, a combination of two or more rubbers is preferred such as cis 1,4-polyisoprene rubber (natural or synthetic, although natural is preferred), 3,4-polyisoprene rubber, styrene/isoprene/butadiene rubber, emulsion and solution polymerization derived styrene/butadiene rubbers, cis 1,4-polybutadiene rubbers and emulsion polymerization prepared butadiene/acrylonitrile copolymers.

In one aspect of this invention, an emulsion polymerization derived styrene/butadiene (E-SBR) might be used having a relatively conventional styrene content of about 20 to about 28 percent bound styrene or, for some applications, an E-SBR having a medium to relatively high bound styrene content, namely, a bound styrene content of about 30 to about 45 percent.

By emulsion polymerization prepared E-SBR, it is meant that styrene and 1,3-butadiene are copolymerized as an aqueous emulsion. Such are well known to those skilled in such art. The bound styrene content can vary, for example, from about 5 to about 50 percent. In one aspect, the E-SBR may also contain acrylonitrile to form a terpolymer rubber, as E-SBAR, in amounts, for example, of about 2 to about 30 weight percent bound acrylonitrile in the terpolymer.

Emulsion polymerization prepared styrene/butadiene/acrylonitrile copolymer rubbers containing about 2 to about 40 weight percent bound acrylonitrile in the copolymer are also contemplated as diene based rubbers for use in this invention.

The solution polymerization prepared SBR (S-SBR) typically has a bound styrene content in a range of about 5 to about 50, preferably about 9 to about 36, percent. The S-SBR can be conveniently prepared, for example, by organo lithium catalyzation in the presence of an organic hydrocarbon solvent.

In one embodiment, cis 1,4-polybutadiene rubber (BR) may be used. Such BR can be prepared, for example, by organic solution polymerization of 1,3-butadiene. The BR may be conveniently characterized, for example, by having at least a 90 percent cis 1,4-content.

The cis 1,4-polyisoprene and cis 1,4-polyisoprene natural rubber are well known to those having skill in the rubber art.

The term "phr" as used herein, and according to conventional practice, refers to "parts by weight of a respective material per 100 parts by weight of rubber, or elastomer."

The rubber composition may also include up to 70 phr of processing oil. Processing oil may be included in the rubber composition as extending oil typically used to extend elastomers. Processing oil may also be included in the rubber composition by addition of the oil directly during rubber compounding. The processing oil used may include both extending oil present in the elastomers, and process oil added during compounding. Suitable process oils include various oils as are known in the art, including aromatic, paraffinic, naphthenic, vegetable oils, and low PCA oils, such as MES, TDAE, SRAE and heavy naphthenic oils. Suitable low PCA oils include those having a polycyclic aromatic content of less than 3 percent by weight as determined by the IP346 method. Procedures for the IP346 method may be found in *Standard Methods for Analysis & Testing of Petroleum and Related Products* and *British Standard* 2000 *Parts,* 2003, 62nd edition, published by the Institute of Petroleum, United Kingdom.

The rubber composition may include from about 10 to about 150 phr of silica. In another embodiment, from 20 to 80 phr of silica may be used.

The commonly employed siliceous pigments which may be used in the rubber compound include conventional pyrogenic and precipitated siliceous pigments (silica). In one embodiment, precipitated silica is used. The conventional siliceous pigments employed in this invention are precipitated silicas such as, for example, those obtained by the acidification of a soluble silicate, e.g., sodium silicate.

Such conventional silicas might be characterized, for example, by having a BET surface area, as measured using nitrogen gas. In one embodiment, the BET surface area may be in the range of about 40 to about 600 square meters per gram. In another embodiment, the BET surface area may be in a range of about 80 to about 300 square meters per gram.

The BET method of measuring surface area is described in the *Journal of the American Chemical Society*, Volume 60, Page 304 (1930).

The conventional silica may also be characterized by having a dibutylphthalate (DBP) absorption value in a range of about 100 to about 400, alternatively about 150 to about 300.

The conventional silica might be expected to have an average ultimate particle size, for example, in the range of 0.01 to 0.05 micron as determined by the electron microscope, although the silica particles may be even smaller, or possibly larger, in size.

Various commercially available silicas may be used, such as, only for example herein, and without limitation, silicas commercially available from PPG Industries under the Hi-Sil trademark with designations 210, 243, etc.; silicas available from Rhodia, with, for example, designations of Z1165MP and Z165GR and silicas available from Degussa AG with, for example, designations VN2 and VN3, etc.

Commonly employed carbon blacks can be used as a conventional filler in an amount ranging from 10 to 150 phr. In another embodiment, from 20 to 80 phr of carbon black may be used. Representative examples of such carbon blacks include N110, N121, N134, N220, N231, N234, N242, N293, N299, N315, N326, N330, N332, N339, N343, N347, N351, N358, N375, N539, N550, N582, N630, N642, N650, N683, N754, N762, N765, N774, N787, N907, N908, N990 and N991. These carbon blacks have iodine absorptions ranging from 9 to 145 g/kg and DBP number ranging from 34 to 150 cm$^3$/100 g.

Other fillers may be used in the rubber composition including, but not limited to, particulate fillers including ultra-high molecular weight polyethylene (UHMWPE), crosslinked particulate polymer gels including but not limited to those disclosed in U.S. Pat. Nos. 6,242,534; 6,207,757; 6,133,364; 6,372,857; 5,395,891; or 6,127,488, and plasticized starch composite filler including but not limited to that disclosed in U.S. Pat. No. 5,672,639. Such other fillers may be used in an amount ranging from 1 to 30 phr.

In one embodiment, the rubber composition may contain a conventional sulfur containing organosilicon compound. In one embodiment, the sulfur containing organosilicon compounds are the 3,3'-bis(trimethoxy or triethoxy silylpropyl) polysulfides. In one embodiment, the sulfur containing organosilicon compounds are 3,3'-bis(triethoxysilylpropyl) disulfide and/or 3,3'-bis(triethoxysilylpropyl) tetrasulfide.

In another embodiment, suitable sulfur containing organosilicon compounds include compounds disclosed in U.S. Pat. No. 6,608,125. In one embodiment, the sulfur containing organosilicon compounds includes 3-(octanoylthio)-1-propyltriethoxysilane, $CH_3(CH_2)_6C(=O)$—S—$CH_2CH_2CH_2Si(OCH_2CH_3)_3$, which is available commercially as NXT™ from Momentive Performance Materials.

In another embodiment, suitable sulfur containing organosilicon compounds include those disclosed in U.S. Patent Publication No. 2003/0130535. In one embodiment, the sulfur containing organosilicon compound is Si-363 from Degussa.

The amount of the sulfur containing organosilicon compound in a rubber composition will vary depending on the level of other additives that are used. Generally speaking, the amount of the compound will range from 0.5 to 20 phr. In one embodiment, the amount will range from 1 to 10 phr.

It is readily understood by those having skill in the art that the rubber composition would be compounded by methods generally known in the rubber compounding art, such as mixing the various sulfur-vulcanizable constituent rubbers with various commonly used additive materials such as, for example, sulfur donors, curing aids, such as activators and retarders and processing additives, such as oils, resins including tackifying resins and plasticizers, fillers, pigments, fatty acid, zinc oxide, waxes, antioxidants and antiozonants and peptizing agents. As known to those skilled in the art, depending on the intended use of the sulfur vulcanizable and sulfur-vulcanized material (rubbers), the additives mentioned above are selected and commonly used in conventional amounts. Representative examples of sulfur donors include elemental sulfur (free sulfur), an amine disulfide, polymeric polysulfide and sulfur olefin adducts. In one embodiment, the sulfur-vulcanizing agent is elemental sulfur. The sulfur-vulcanizing agent may be used in an amount ranging from 0.5 to 8 phr, alternatively with a range of from 1.5 to 6 phr. Typical amounts of tackifier resins, if used, comprise about 0.5 to about 10 phr, usually about 1 to about 5 phr. Typical amounts of processing aids comprise about 1 to about 50 phr. Typical amounts of antioxidants comprise about 1 to about 5 phr. Representative antioxidants may be, for example, diphenyl-p-phenylenediamine and others, such as, for example, those disclosed in *The Vanderbilt Rubber Handbook* (1978), Pages 344 through 346. Typical amounts of antiozonants comprise about 1 to 5 phr. Typical amounts of fatty acids, if used, which can include stearic acid comprise about 0.5 to about 3 phr. Typical amounts of zinc oxide comprise about 2 to about 5 phr. Typical amounts of waxes comprise about 1 to about 5 phr. Often microcrystalline waxes are used. Typical amounts of peptizers comprise about 0.1 to about 1 phr. Typical peptizers may be, for example, pentachlorothiophenol and dibenzamidodiphenyl disulfide.

Accelerators are used to control the time and/or temperature required for vulcanization and to improve the properties of the vulcanizate. In one embodiment, a single accelerator system may be used, i.e., primary accelerator. The primary accelerator(s) may be used in total amounts ranging from about 0.5 to about 4, alternatively about 0.8 to about 1.5, phr. In another embodiment, combinations of a primary and a secondary accelerator might be used with the secondary accelerator being used in smaller amounts, such as from about 0.05 to about 3 phr, in order to activate and to improve the properties of the vulcanizate. Combinations of these accelerators might be expected to produce a synergistic effect on the final properties and are somewhat better than those produced by use of either accelerator alone. In addition, delayed action accelerators may be used which are not affected by normal processing temperatures but produce a satisfactory cure at ordinary vulcanization temperatures. Vulcanization retarders might also be used. Suitable types of accelerators that may be used in the present invention are amines, disulfides, guanidines, thioureas, thiazoles, thiurams, sulfenamides, dithiocarbamates and xanthates. In one embodiment, the primary accelerator is a sulfenamide. If a second accelerator is used, the secondary accelerator may be a guanidine, dithiocarbamate or thiuram compound.

The mixing of the rubber composition can be accomplished by methods known to those having skill in the rubber mixing art. For example, the ingredients are typically mixed in at least two stages, namely, at least one non-productive stage followed by a productive mix stage. The final curatives including sulfur-vulcanizing agents are typically mixed in the final stage which is conventionally called the "productive" mix stage in which the mixing typically occurs at a temperature, or ultimate temperature, lower than the mix temperature(s) than the preceding non-productive mix stage(s). The terms "non-productive" and "productive" mix stages are well known to those having skill in the rubber mixing art. The rubber composition may be subjected to a thermomechanical mixing step. The thermomechanical mixing step generally comprises a mechanical working in a mixer or extruder for a period of time suitable in order to produce a rubber temperature between 140° C. and 190° C. The appropriate duration of the thermomechanical working varies as a function of the operating conditions, and the volume and nature of the components. For example, the thermomechanical working may be from 1 to 20 minutes.

The rubber composition may be incorporated in a variety of rubber components of the tire. For example, the rubber component may be a tread (including tread cap and tread base), sidewall, apex, chafer, sidewall insert, wirecoat or innerliner. In one embodiment, the component is a tread.

Alternatively, the rubber composition may be used in various manufactured items including but not limited to tire treads, shoes, shoe soles, transmission belts, hoses, airsprings, conveyor belts, track belts, and vibration isolators.

The pneumatic tire of the present invention may be a race tire, passenger tire, aircraft tire, agricultural, earthmover, off-the-road, truck tire, and the like. In one embodiment, the tire is a passenger or truck tire. The tire may also be a radial or bias.

Vulcanization of the pneumatic tire of the present invention is generally carried out at conventional temperatures ranging from about 100° C. to 200° C. In one embodiment, the vulcanization is conducted at temperatures ranging from about 110° C. to 180° C. Any of the usual vulcanization processes may be used such as heating in a press or mold, heating with superheated steam or hot air. Such tires can be built, shaped, molded and cured by various methods which are known and will be readily apparent to those having skill in such art.

This invention is illustrated by the following examples that are merely for the purpose of illustration and are not to be regarded as limiting the scope of the invention or the manner in which it can be practiced. Unless specifically indicated otherwise, parts and percentages are given by weight.

EXAMPLES

General Experimental

For internal illumination: A glass UV reactor was used for photocatalytic thiol-ene reactions. The reactor was equipped with a water-cooled, jacketed internal illumination well. The light source was a medium pressure, Hg vapor lamp. The Hg lamp was fitted with a Pyrex Absorp Sleeve to eliminate wavelengths below ~300 nm.

For external illumination: A glass bottle was used for photocatalytic thiol-ene reactions. The light source was a medium pressure, Hg vapor lamp. The Hg lamp was fitted with a Pyrex Absorp Sleeve to eliminate wavelengths below ~300 nm. The light source was placed inside a water-cooled, jacketed illumination well, which was then positioned adjacent to the bottle during the reaction to allow for full illumination.

Example 1. Synthesis of HOSBO-HDT$_2$

High oleic soybean oil (200 g, 0.227 mol), 1,6-hexanedithiol (3 eq, 104.3 mL, 0.682 mol), and 1173 (2-hydroxy-2-methylpropiophenone; 2 wt %, 3.6 mL) were added to the UV reactor neat. The reaction mixture was vigorously stirred with internal illumination at room temperature for 3 hours. After this time, $^1$H NMR analysis showed complete consumption of the olefin content, but only an average of 2 free thiols per triglyceride. The remaining olefin content was consumed by cross-linking arising from 1,6-hexanedithiol reacting twice.

Example 2. Synthesis of HOSBO-HDT$_3$ 1,6-Hexandithiol and 1173 (2-hydroxy-2-methylpropiophenone; 2 wt %, 7.8 g) were combined and stirred vigorously. High oleic soybean oil (391.1 g, 444.86 mmol) was added to a liquid addition funnel, the reaction was illuminated, and the oil was added as a slow stream. The reaction was stirred with external illumination for 5 h. A visible lack of gel formation was noted compared to HOSBO-HDT$_2$, and GPC confirmed that the material was not dimeric. $^1$H NMR confirmed complete olefin consumption, with an average of 3 free thiols per triglyceride.

Example 3. Synthesis of HOSBO-HDT$_x$

High oleic soybean oil (5.0 g, 5.69 mmol), 1,6-hexanedithiol (1 eq, 0.870 mL, 5.69 mmol), and 1173 (2-hydroxy-2-methylpropiophenone; 2 wt %, 90.3 µL) were added to the UV reactor neat. The reaction mixture was stirred with external illumination at room temperature. After 1 hour, $^1$H NMR analysis showed that 27% of the olefin content had been thiolated. After 3 hours, $^1$H NMR analysis showed that 42% of the olefin content had been thiolated. To prevent crosslinking from continued reactivity once the desired functionalization level is attained, the radical must be quenched.

Example 4. Synthesis of MPTES-SS-Bt 2,2'-Dithiobis-benzothiazole (139.65 g, 420.0 mmol) was suspended in 750 mL dry CHCl$_3$. MPTES (mercaptopropyltriethoxysilane) was dissolved separately in 750 mL dry CHCl$_{13}$ and added dropwise to the 2,2'-Dithiobis-benzothiazole suspension over 16 h (2.0 mL/min) at ambient temperature. The reaction was stirred an additional 9 h at ambient temperature, at which point the reaction mixture was concentrated to precipitate any MBT and Bt-SH. A large amount of hexane was added, and the crude product was filtered through a pad of celite and Na$_2$SO$_4$, washed with hexane, and concentrated to give the pure product as a translucent, brown liquid (140.7 g, 99% purity, 99.6% yield). The product was stored in the freezer for future use.

Example 5. Synthesis of HOSBO-HDT-MPTES **HOSBO-HDT-

HOSBO-HDT from Example 2 (75 g, 58.03 mmol) was dissolved in dry CHC13 (750 mL) in a 1 L flask. In a separate, 3 L flask, MPTES-SS-Bt from Example 4 (70.3 g, 174.08 mmol, 3 eq) was dissolved in dry CHC13 (750 mL) and stirred vigorously. Addition was started immediately via syringe pump (6.25 mL/min) and continued for 2 h. The reaction was stirred an additional 19.5 h at ambient temperature. Due to the disproportionation of MPTES-SS-Bt to 2,2'-dithiobis-benzothiazole at ambient temperature, another aliquot of MPTES-SS-Bt (5.86 g, 14.51 mmol) was added, and the reaction was stirred a further 2 days to completion. The reaction was concentrated to give the crude product, which was taken up in hexane and filtered to remove any 2,2'-dithiobis-benzothiazole side product. The filtrate was concentrated to give the pure product as a yellow oil (93.9 g, 99% purity, 82% yield).

Example 6. Mixing of Rubber Compounds

The rubber compounds were mixed in a 360 g Haake mixer, using 100 phr of 70/30 wt/wt styrene-butadiene and polybutadiene rubbers, 65 phr silica, 0-20 phr oil, 0-20 phr HOSBO-HDT-MPTES from Example 5, 11.5 phr additives including curatives and processing aids, and 0-6.5 phr bis(triethoxysilylpropyl) disulfide, (Si266 from Evonik) in the first stage. The first stage was mixed for 2 minutes at 160° C. The final stage of mixing used 0.5-1.5 phr sulfur and 2.25 phr curatives. Samples were cured at 160° C. for 20 minutes. Adjustments to oil and Si266 levels were made based on calculations to compensate for excesses of these materials as the experimental soy-silane (HOSBO-HDT-MPTES) levels were varied.

| Stage 1 - 2 min, 160° C. | |
|---|---|
| Polymer | 100 phr |
| Silica | 65 phr |
| Oil | 0-31.5 phr |
| Additives | 11.5 phr |
| Si266 | 0-6.5 |

| Stage 2 | |
|---|---|
| Sulfur | 1.5 phr |
| Curatives | 4.25 phr |

RPA, MDR, tensile, and extraction data were obtained on the samples. Cryo-milled compound samples were extracted by Accelerated Solvent Extraction (ASE) using acetone. Composition of the extracted residues was confirmed by NMR. The relevant data is reported in the following tables.

| RPA & MDR Data | | | | | | |
|---|---|---|---|---|---|---|
| HOSBO-HDT-MPTES | — | 10.0 | 10.0 | 10.0 | 10.0 | 20.0 |
| Oil | 20.0 | 20.0 | 20.0 | 10.0 | 20.0 | 20.0 |
| Si266 | 6.50 | 6.50 | 4.76 | 4.76 | — | — |
| T90 | 11.6 | 11.5 | 11.0 | 11.0 | 9.23 | 11.4 |
| S' max | 20.0 | 22.5 | 21.3 | 26.5 | 18.3 | 19.8 |
| Δ torque | 16.9 | 19.9 | 18.6 | 23.0 | 14.7 | 16.5 |
| Uncured G' (0.833 Hz) | 201 | 210 | 231 | 293 | 280 | 278 |
| Tensile Data | | | | | | |
| TS5 | 9.2 | 3.7 | 4.3 | 3.7 | 6.20 | 2.99 |
| Elongation at break | 500 | 354 | 368 | 315 | 468 | 335 |
| M100 | 2.25 | 3.78 | 3.44 | 4.57 | 3.18 | 4.54 |
| M300 | 7.65 | 12.1 | 11.3 | 15.5 | 10.8 | 13.9 |

| Extraction Data | | |
|---|---|---|
| | Si266 | No Si266 |
| Extracted HOSBO-HDT-MPTES (%) | 0-1 | 18-30 |
| Retained HOSBO-HDT-MPTES (%) | 99-100 | 70-82 |

Significance

The above data demonstrates the utility of 3-mercaptopropyltriethoxysilanedisulfide-functionalized soybean oil. Comparing the compound data to the control, it is observed that the addition of HOSBO-HDT-MPTES increases the uncured compound stiffness (uncured G') only very slightly. Upon partial removal of silica coupling/hydrophobating agent Si266, the uncured stiffness increases slightly again. Complete removal of Si266 gives increased compound stiffness. Therefore, either removing oil or coupling agent from the mix results in an increase in compound stiffness, which is expected. However, when coupler Si266 is either partially or completely removed from the mix, there is an increase in cross-link density compared to the control, exhibited by the corresponding increase in the 300% modulus. This effect is amplified by the inclusion of more HOSBO-HDT-MPTES.

One effect of Si266 is demonstrated by the comparison of the extraction data to the final compound stiffness (S'max). When Si266 remained in the mix, the final stiffness was increased up to 33% more than the control, which agrees with an increase in crosslink density shown by the 300% modulus data as well as the lack of ability to extract the HOSBO-HDT-MPTES from the cured compound. This means that the HOSBO-HDT-MPTES has been cured into the final compound matrix.

If Si266 is completely removed from the mix, the uncured compound stiffness is higher as the silica is no longer hydrophobated as effectively. The absence of Si266 also effects the ability of HOSBO-HDT-MPTES to cure into the final compound. This is evident due to the larger amount of HOSBO-HDT-MPTES extracted from the final compound and the relatively unchanged S'$_{max}$ from the control compound.

It can be therefore be concluded that HOSBO-HDT-MPTES can be used to create a silica compound with good processability (uncured G') and much higher cured stiffness (S'$_{max}$) as a result of increased crosslink density. The elongation at break decreases as a result of this stiffness change, but can be recovered and adjusted to an extent by manipulating the oil, Si266, and other additive content.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

What is claimed is:

1. A vegetable oil derivative comprising the structure

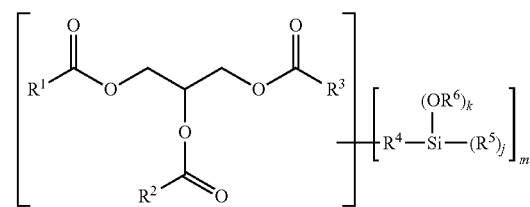

where $R^1$, $R^2$, and $R^3$ are independently C15-C20 alkenyl, C15-C20 alkyl, and optionally containing aromatic groups; $R^4$ is —S—S—$R^7$— or $R^4$ is —S—X—S—

S—R⁷— where X is unsubstituted C1 to C10 alkane diyl; R⁵, R⁶ are independently C1 to C10 alkyl, R⁷ is C1 to C10 alkane diyl, j=0 to 2, k=1 to 3, and j+k=3; wherein each R⁴ is attached via a carbon-sulfur linkage to one of R¹, R² or R³; and m is the number of the carbon-sulfur linkages based on olefinic unsaturation of R¹, R² and R³.

2. The vegetable oil derivative of claim 1 comprising the structure

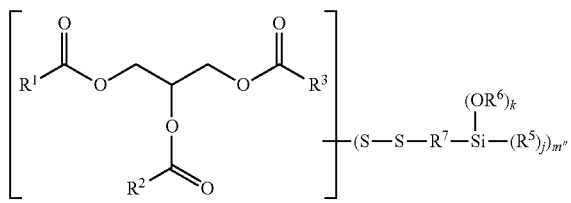

where m" is the number of the carbon-sulfur linkages based on olefinic unsaturation of R¹, R² and R³.

3. The vegetable oil derivative of claim 1 comprising the structure

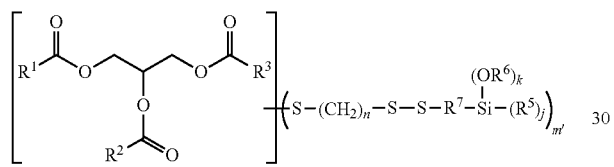

where m' is the number of the carbon-sulfur linkages based on olefinic unsaturation of R¹, R² and R³ and n is 1 to 6.

4. The vegetable oil derivative of claim 1 wherein the vegetable oil is selected from the group consisting of soybean oils, canola oils, castor oils, palm oils, coconut oil, and corn oils.

5. The vegetable oil derivative of claim 1 wherein the vegetable oil is a high oleic soybean oil comprising about 75 percent by weight oleic acid residues.

6. The vegetable oil derivative of claim 4 wherein R¹, R², and R³ together comprise about 75 weight percent oleyl groups.

7. A vulcanizable rubber composition comprising the vegetable oil derivative of claim 1.

8. A vulcanizable rubber composition comprising the vegetable oil derivative of claim 4.

9. A pneumatic tire comprising the vulcanizable rubber composition of claim 7.

10. A manufactured item comprising the vulcanizable rubber composition of claim 7 wherein the manufactured item is selected from the group consisting of tire treads, shoes, shoe soles, transmission belts, hoses, airsprings, conveyor belts, track belts, and vibration isolators.

11. A method of making a vegetable oil derivative comprising the steps of:
obtaining a thiolized triglyceride; and
reacting the thiolized triglyceride with a silane disulfide comprising a silyl group at one terminus and a leaving group at the other terminus, to produce the vegetable oil derivative.

12. The method of claim 11 wherein the thiolized triglyceride is of the formula

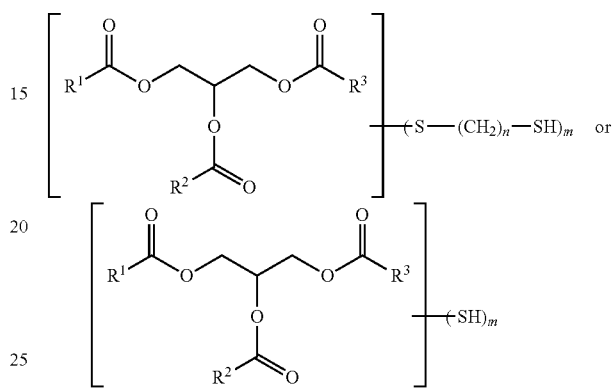

where R¹, R², and R³ are independently C15-C20 alkenyl, C15-C20 alkyl, and optionally containing aromatic groups; n is from 1 to 6; each S—(CH₂)ₙ—SH or —SH is covalently bonded to a carbon atom of one of R¹, R² or R³; and m is the number of —S—(CH²)ₙ—SH or —SH groups based on olefinic unsaturation of R¹, R² and R³.

13. The method of claim 11 wherein the silane disulfide is of formula

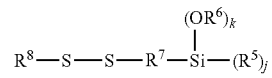

where R⁵, R⁶ are independently C1 to C10 alkyl, R⁷ is C1 to C10 alkane diyl, j=0 to 2, k=1 to 3, and j+k=3, and R⁸ is an organic leaving group.

14. The method of claim 13 wherein R⁸ is a benzothiazolyl group.

15. The method of claim 11 wherein the silane disulfide is 2-[[3-triethoxysilyl)propyl]dithio]benzothiazole.

16. The method of claim 11 wherein the triglyceride is a vegetable oil selected from the group consisting of soybean oils, canola oils, castor oils, palm oils, coconut oil, and corn oils.

17. The method of claim 11 wherein the triglyceride is a high oleic soybean oil comprising about 75 percent by weight of oleic acid residues.

\* \* \* \* \*